US010413404B2

(12) United States Patent
Benichou

(10) Patent No.: US 10,413,404 B2
(45) Date of Patent: *Sep. 17, 2019

(54) LEAFLET ATTACHMENT FRAME FOR A PROSTHETIC VALVE

(71) Applicant: Edwards Lifesciences Corporation, Irvine, CA (US)

(72) Inventor: Netanel Benichou, D.N. Hof HaCarmel (IL)

(73) Assignee: Edwards Lifesciences Corporation, Irvine, CA (US)

(*) Notice: Subject to any disclaimer, the term of this patent is extended or adjusted under 35 U.S.C. 154(b) by 89 days.

This patent is subject to a terminal disclaimer.

(21) Appl. No.: 15/367,092

(22) Filed: Dec. 1, 2016

(65) Prior Publication Data

US 2017/0079788 A1    Mar. 23, 2017

Related U.S. Application Data

(63) Continuation of application No. 12/335,461, filed on Dec. 15, 2008, now Pat. No. 9,510,942.

(60) Provisional application No. 61/014,007, filed on Dec. 14, 2007.

(51) Int. Cl.
*A61F 2/24* (2006.01)

(52) U.S. Cl.
CPC .......... *A61F 2/2418* (2013.01); *A61F 2/2412* (2013.01); *A61F 2/2415* (2013.01); *A61F 2/2409* (2013.01); *A61F 2210/0076* (2013.01); *A61F 2220/0075* (2013.01); *A61F 2230/0054* (2013.01)

(58) Field of Classification Search
None
See application file for complete search history.

(56) References Cited

U.S. PATENT DOCUMENTS

| 3,409,013 A | 11/1968 | Berry |
| 3,548,417 A | 12/1970 | Kisher |
| 3,570,014 A | 3/1971 | Hancock |
| 3,587,115 A | 6/1971 | Shiley |
| 3,657,744 A | 4/1972 | Ersek |

(Continued)

FOREIGN PATENT DOCUMENTS

| DE | 2246526 A1 | 3/1973 |
| DE | 19532846 A1 | 3/1997 |

(Continued)

OTHER PUBLICATIONS

Extended European Search Report, EP13002630, dated Jul. 1, 2013.

(Continued)

*Primary Examiner* — Thomas Sweet
*Assistant Examiner* — Megan Y Wolf
(74) *Attorney, Agent, or Firm* — Klarquist Sparkman, LLC; Joel B. German

(57) ABSTRACT

An implantable prosthetic valve has an upper frame section and a lower frame section. The upper frame section has a plurality of struts and a first leaflet receiving surface at a lower portion of the upper frame section. The lower frame section has a second leaflet receiving surface at an upper portion of the lower frame section. An edge of a flexible leaflet is disposed between the first and second leaflet receiving surfaces to attach the leaflet to the upper and lower frame sections.

19 Claims, 8 Drawing Sheets

(56) References Cited

U.S. PATENT DOCUMENTS

| | | |
|---|---|---|
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |

(56) References Cited

U.S. PATENT DOCUMENTS

| | | | |
|---|---|---|---|
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,075,611 B2 | 12/2011 | Millwee et al. | |
| 8,128,686 B2 | 3/2012 | Paul et al. | |
| 8,167,932 B2 | 5/2012 | Bourang | |
| 8,291,570 B2 | 10/2012 | Eidenschink | |
| 8,348,998 B2 | 1/2013 | Pintor | |
| 8,449,606 B2 | 5/2013 | Eliasen et al. | |
| 8,454,685 B2 | 6/2013 | Hariton | |
| 8,652,203 B2 | 2/2014 | Quadri | |
| 8,747,463 B2 | 6/2014 | Fogarty et al. | |
| 9,510,942 B2 * | 12/2016 | Benichou | A61F 2/2412 |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0143390 A1 | 10/2002 | Ishii | |
| 2002/0173842 A1 | 11/2002 | Buchanan | |
| 2003/0014105 A1 | 1/2003 | Cao | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0024452 A1 | 2/2004 | Kruse et al. | |
| 2004/0039436 A1 | 2/2004 | Spenser et al. | |
| 2004/0078074 A1 | 4/2004 | Anderson et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0225356 A1 * | 11/2004 | Frater | A61F 2/2409 623/2.14 |
| 2004/0260389 A1 | 12/2004 | Case et al. | |
| 2005/0010285 A1 | 2/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0096738 A1 | 5/2005 | Cali et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0149350 A1 | 7/2006 | Patel et al. | |
| 2006/0183383 A1 | 8/2006 | Asmus et al. | |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0208550 A1 | 9/2007 | Cao et al. | |
| 2007/0213813 A1 | 9/2007 | von Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0021546 A1 | 7/2008 | Patz et al. | |
| 2008/0183271 A1 | 7/2008 | Frawley et al. | |
| 2008/0208327 A1 | 8/2008 | Rowe | |
| 2008/0243245 A1 | 10/2008 | Thamber et al. | |
| 2008/0255660 A1 | 10/2008 | Guyenot et al. | |
| 2008/0275537 A1 | 11/2008 | Limon | |
| 2008/0294248 A1 | 11/2008 | Yang et al. | |
| 2009/0118826 A1 | 5/2009 | Khaghani | |
| 2009/0125118 A1 | 5/2009 | Gong | |
| 2009/0157175 A1 | 6/2009 | Benichou | |
| 2009/0276040 A1 | 11/2009 | Rowe | |
| 2009/0281619 A1 | 11/2009 | Le et al. | |
| 2009/0287296 A1 | 11/2009 | Manasse | |
| 2009/0287299 A1 | 11/2009 | Tabor et al. | |
| 2009/0299452 A1 | 12/2009 | Eidenschink et al. | |
| 2009/0319037 A1 | 12/2009 | Rowe et al. | |
| 2010/0049313 A1 | 2/2010 | Alon et al. | |
| 2010/0168844 A1 | 4/2010 | Toomes et al. | |
| 2010/0185277 A1 | 4/2010 | Braido et al. | |
| 2010/0082094 A1 | 7/2010 | Quadri et al. | |
| 2010/0198347 A1 | 8/2010 | Zakay et al. | |
| 2010/0204781 A1 | 8/2010 | Alkhatib | |
| 2011/0015729 A1 | 1/2011 | Jimenez et al. | |
| 2011/0022157 A1 | 1/2011 | Essinger et al. | |
| 2011/0066224 A1 | 3/2011 | White | |
| 2011/0137397 A1 | 6/2011 | Chau et al. | |
| 2011/0218619 A1 | 9/2011 | Benichou et al. | |
| 2011/0319991 A1 | 12/2011 | Hariton et al. | |
| 2012/0089223 A1 | 4/2012 | Nguyen et al. | |
| 2012/0101571 A1 | 4/2012 | Thamber et al. | |
| 2012/0123529 A1 | 5/2012 | Levi et al. | |
| 2012/0259409 A1 | 10/2012 | Nguyen et al. | |
| 2013/0023985 A1 | 1/2013 | Khairkhahan et al. | |
| 2013/0046373 A1 | 2/2013 | Cartledge et al. | |
| 2013/0150956 A1 | 6/2013 | Yohanan et al. | |
| 2013/0166017 A1 | 6/2013 | Cartledge et al. | |
| 2013/0190857 A1 | 7/2013 | Mitra et al. | |
| 2013/0274873 A1 | 10/2013 | Delaloye et al. | |
| 2013/0310926 A1 | 11/2013 | Hariton | |
| 2013/0317598 A1 | 11/2013 | Rowe et al. | |
| 2013/0331929 A1 | 12/2013 | Mitra et al. | |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0277563 A1 | 9/2014 | White | |
| 2014/0296962 A1 | 10/2014 | Cartledge et al. | |
| 2014/0330372 A1 | 11/2014 | Weston et al. | |
| 2014/0343670 A1 | 11/2014 | Bakis et al. | |
| 2014/0343671 A1 | 11/2014 | Yohanan et al. | |
| 2014/0350667 A1 | 11/2014 | Braido et al. | |
| 2015/0073545 A1 | 3/2015 | Braido | |
| 2015/0073546 A1 | 3/2015 | Braido | |
| 2015/0135506 A1 | 5/2015 | White | |
| 2015/0157455 A1 | 6/2015 | Hoang et al. | |
| 2017/0014229 A1 | 1/2017 | Nguyen-Then-Nhon et al. | |
| 2018/0028310 A1 | 2/2018 | Gurovich et al. | |
| 2018/0153689 A1 | 6/2018 | Maimon et al. | |
| 2018/0325665 A1 | 11/2018 | Gurovich et al. | |
| 2018/0344456 A1 | 12/2018 | Barash et al. | |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0597967 A1 | 5/1994 |
| EP | 0592410 B1 | 10/1995 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 1796597 | 6/2007 |
| FR | 2788217 A1 | 7/2000 |
| FR | 2815844 | 5/2002 |
| GB | 2056023 A | 3/1981 |
| SU | 1271508 A1 | 11/1986 |
| WO | 1991017720 A1 | 11/1991 |

(56) References Cited

FOREIGN PATENT DOCUMENTS

| | | |
|---|---|---|
| WO | 92/17118 A1 | 10/1992 |
| WO | 1993001768 A1 | 2/1993 |
| WO | 1997024080 | 7/1997 |
| WO | 1998029057 A1 | 7/1998 |
| WO | 1999030646 | 6/1999 |
| WO | 99/33414 A1 | 7/1999 |
| WO | 1999040964 A1 | 8/1999 |
| WO | 1999047075 A1 | 9/1999 |
| WO | 2000018333 | 4/2000 |
| WO | 00/41652 A1 | 7/2000 |
| WO | 00/47139 A1 | 8/2000 |
| WO | 01/35878 A2 | 5/2001 |
| WO | 01/49213 A2 | 7/2001 |
| WO | 01/54625 A1 | 8/2001 |
| WO | 01/62189 A1 | 8/2001 |
| WO | 2001054624 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 2003047468 | 6/2003 |
| WO | 2005034812 | 4/2005 |
| WO | 2005055883 | 6/2005 |
| WO | 2005084595 | 9/2005 |
| WO | 2005102015 A2 | 11/2005 |
| WO | 2006014233 | 2/2006 |
| WO | 2006032051 | 3/2006 |
| WO | 2006034008 | 3/2006 |
| WO | 2006108090 | 10/2006 |
| WO | 2006108090 A2 | 10/2006 |
| WO | 2006111391 | 10/2006 |
| WO | 2006127089 | 11/2006 |
| WO | 2006138173 | 12/2006 |
| WO | 2007047488 | 4/2007 |
| WO | 2007067942 | 6/2007 |
| WO | 2007097983 | 8/2007 |
| WO | 2008005405 | 1/2008 |
| WO | 2008015257 | 2/2008 |
| WO | 2008035337 | 3/2008 |
| WO | 2008091515 | 7/2008 |
| WO | 08/147964 A1 | 12/2008 |
| WO | 08/150529 A1 | 12/2008 |
| WO | 2009033469 | 3/2009 |
| WO | 2009042196 | 4/2009 |
| WO | 2009053497 | 4/2009 |
| WO | 2009061389 | 5/2009 |
| WO | 2009116041 A2 | 9/2009 |
| WO | 2009149462 | 12/2009 |
| WO | 2010011699 | 1/2010 |
| WO | 2010121076 | 10/2010 |
| WO | 2013106585 | 7/2013 |
| WO | 2015085218 | 6/2015 |

OTHER PUBLICATIONS

Andersen et al., "Transluminal Implantation of Artificial Heart Valves. Description of a New Expandable Aortic Valve and Initial Results with Implantation by Catheter Technique in Closed Chest Pigs" European Heart Journal, 1992, 13, 704-708.

Andersen, Henning Rud, History of Percutaneous Aortic Valve Prosthesis, Herz 34 2009 Nr. 5, Urban & Vogel, pp. 343-346, Skejby University Hospital Department of Cardiology, Aarhus, Denmark.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

* cited by examiner

LEAFLET ATTACHMENT FRAME FOR A PROSTHETIC VALVE

CROSS REFERENCE TO RELATED APPLICATIONS

This application is a continuation of U.S. patent application Ser. No. 12/335,461, filed on Dec. 15, 2008, now U.S. Pat. No. 9,510,942, which claims the benefit of U.S. Provisional Application No. 61/014,007, filed on Dec. 14, 2007. Both of which are incorporated herein by reference.

FIELD

The present disclosure relates generally to an apparatus and method for the restoration of heart valve function. More particularly, the present disclosure concerns embodiments of an implantable prosthetic valve and methods for making the same.

BACKGROUND

Prosthetic cardiac valves have been used for many years to treat various cardiac valvular disorders. For many years, the definitive treatment was the surgical repair or replacement of a native valve during open heart surgery. More recently, transvascular techniques have been developed, which reduce or eliminate many of the undesirable complications of open heart surgery. Such transvascular techniques traditionally involve the implantation of a prosthetic valve that can be compressed or folded to a reduced diameter. By compressing or folding the prosthetic valve to a reduced diameter, the prosthetic valve can be delivered through a less invasive penetration to a desired target location within the human anatomy. Thereafter, the compressed valve is traditionally released, expanded, separated from the delivery system, and secured to the desired target location.

SUMMARY

A valve prosthesis is provided which is suitable for implantation in body channels or ducts. The valve prosthesis includes an implantable structure having a deployable construction adapted to be initially crimped in a narrow configuration suitable for catheterization through the body ducts to a target location and adapted to be deployed by exerting substantially radial forces (or releasing the valve, if the valve is self-expandable) from within by means of a deployment device to a deployed state at the target location.

The valve prosthesis desirably includes a two-part foldable frame. The frame is configured to support the flexible leaflets of a unidirectional valve in an optimal manner. The frame has an "upper part" and a "lower part" wherein each part of the frame is shaped with rounded arc portions to support the leaflets. The leaflets are sandwiched between the upper and lower arcs. The frame can have portions, e.g., leaflet receiving portions, that are scalloped shaped to match the shape of the flexible leaflets.

The length of the arcs is matched to the total length of the cell struts that create the frame. The geometrical constraint on the length of the cell struts is such that the frame can be evenly crimped.

In one aspect of the invention, a cloth is first assembled (sewn) to the leaflets. The leaflets with the cloth are sandwiched between the two arcs and the cloth is wrapped over the arcs and sewn together. This suture line crosses all the fabric layers of the wrapped over cloth as well as the leaflet to create a robust leaflet attachment.

In one embodiment, an implantable prosthetic device is provided. The device comprises an upper frame section having a plurality of struts and a first leaflet receiving surface at a lower portion of the upper frame section, a lower frame section having a second leaflet receiving surface at an upper portion of the lower frame section, and at least one flexible leaflet with a first edge portion. The first edge portion is disposed between the first and second leaflet receiving surfaces. In specific implementations, the first and second leaflet receiving surfaces are scalloped shaped.

In other specific implementations, the device further comprises one or more cloth portions that are attached to the flexible leaflet at or near the first edge portion and wrapped around at least a portion of one or both of the first and second receiving surfaces to secure the flexible leaflet to the upper and lower frame sections. The cloth portions can be attached to the flexible leaflet so that a first excess cloth portion extends away from the first edge portion on an upper side of the flexible leaflet and a second excess cloth portion extends away from the first edge portion on a lower side of the flexible leaflet. The first and second excess cloth portions can be wrapped around the respective first and second leaflet receiving surface and secured to one another. In other specific implementations, the upper frame section and the lower frame section can be connected via one or more struts.

In other specific implementations, the upper and lower frame sections can be configured to be expanded from a first configuration to a second configuration. The lengths of the first and second leaflet receiving surfaces can be substantially the same in both the first and second configurations. In other specific implementations, the first leaflet receiving surface comprises an arc section. The arc section can be defined as a portion of the leaflet receiving surface that is located between one or more struts that extend away from the first leaflet receiving surface. The length of the arc section can be substantially equal to the combined length of one or more struts on the upper frame section.

In another embodiment, an implantable prosthetic device comprises a frame comprising a plurality of frame sections. Each frame section can have a lower portion with a scalloped shape. A flexible membrane can comprise a plurality of flexible leaflets, with each flexible leaflet having a lower portion with a scalloped shape. The lower portion of each flexible leaflet can be attached to the lower portion of each frame section.

In specific implementations, the lower portion of each frame section comprises a first part and a second part, the first and second parts being spaced apart to receive the lower portion of the flexible leaflets in an opening formed therebetween. In other specific implementations, one or more cloth portions are attached to each flexible leaflet, and the cloth portions are wrapped around at least a portion of the first and second parts to secure the flexible leaflets to the frame.

In other specific implementations, the frame further comprises first and second vertical posts at an upper area between two frame sections. The two vertical posts can be spaced apart so that they define an opening for receiving a first portion of a first flexible leaflet and a second portion of a second flexible leaflet. Both the first and second portions can be attached to a first and second cloth portion, respectively. The first and second cloth portions can be wrapped around at least a portion of the first and second vertical posts, respectively, to attach the flexible leaflets to the frame. In other specific implementations, a third cloth portion can be positioned radially outside of the frame. The first and second leaflets can be secured to the frame by attaching the first and second cloth portions to the third cloth portion.

In another embodiment, a method is provided for assembling an implantable prosthetic valve comprising a flexible membrane and crimpable frame with an upper and lower part. The method comprises partially crimping the frame to have a diameter that is less than the diameter of the frame when the valve is expanded to its functional size, positioning an edge of the flexible membrane between the upper and lower part of the frame, and securing the edge of the flexible membrane to both the upper and lower part of the frame.

In specific implementations, the method further comprises attaching a cloth portion to the edge of the flexible leaflet so that a first excess cloth portion extends away from the edge on an upper side of the flexible membrane and a second excess cloth portion extends away from the edge on a lower side of the flexible membrane. The first excess cloth portion can be wrapped around at least a portion of the upper part of the frame and the second excess cloth portion can be wrapped around at least a portion of the lower part of the frame. The first and second excess cloth portions can be secured to each other at an area radially outside of the frame.

In another embodiment an implantable prosthetic valve comprises a radially collapsible and expandable annular frame, a leaflet structure positioned within the frame. The frame comprises a plurality of struts and has an upper end and a lower end. The struts are arranged to form a plurality of circumferentially extending rows of closed cells, including an uppermost row of closed cells defining the upper end of the frame. The leaflet structure comprises a plurality of leaflets each comprising two opposing leaflet side portions, each leaflet side portion being paired with an adjacent leaflet side portion of an adjacent leaflet to form commissures of the leaflet structure. The frame comprises a pair of vertical posts adjacent each of the commissures, the vertical posts of each pair being parallel to each other and spaced apart from each other so as to define an opening therebetween. The vertical posts of each pair are connected to each other at their upper ends. The pairs of vertical posts have respective lower ends that are axially spaced from the lower end of the frame. The pairs of vertical posts are positioned axially along the frame entirely within the uppermost row of closed cells, and the pairs of vertical posts are circumferentially spaced apart from each other by a plurality of closed cells of the uppermost row of closed cells. The uppermost row of closed cells is formed partly by an uppermost, circumferentially extending row of angled struts of the frame interconnecting adjacent pairs of vertical posts. The angled struts of the uppermost row of angled struts are connected to each other at their upper ends by U-shaped connection portions. Each U-shaped connection portion forms a gap between adjacent upper ends of a corresponding pair of angled struts. Each pair of leaflet side portions extends radially outwardly through the opening of a respective pair of vertical posts, with one of the leaflet side portions wrapping around at least a portion of one of the vertical posts at a location outside of the frame and the other leaflet side portion wrapping around at least a portion of the other vertical post at a location outside of the frame. Each commissure comprises a cloth portion positioned radially outward of the frame at each pair of vertical posts and radially outward of the leaflet side portions that are wrapped around the vertical posts, the cloth portion also being sutured to the leaflet side portions that are wrapped around the vertical posts.

In some embodiments, each U-shaped connection portion comprises two vertical surfaces and a lateral surface extending between the two vertical surfaces. The vertical surfaces are parallel to a central longitudinal axis of the prosthetic valve, the lateral surface extends between and interconnects upper ends of the vertical surfaces, and the vertical surfaces are spaced apart from each other to define the gap of the U-shaped connection portion.

In some embodiments, the plurality of circumferentially extending rows of closed cells includes additional rows of closed cells that are positioned axially below the uppermost row of closed cells and the pairs of vertical posts.

The foregoing and other objects, features, and advantages of the invention will become more apparent from the following detailed description, which proceeds with reference to the accompanying figures.

DETAILED DESCRIPTION

The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled items.

As used herein, the "expanded" or "deployed" state of a valve assembly or frame refers to the state of the valve assembly/frame when radially expanded to its functional size. The "crimped", "compressed" or "folded" state of a valve assembly or frame refers to the state of the valve assembly/frame when radially compressed or collapsed to a diameter suitable for delivering the valve assembly through a patient's vasculature on a catheter or equivalent mechanism. A valve assembly/frame that is "partially crimped" or "partially compressed" has a diameter that is less than the diameter of the valve assembly/frame in the expanded state and greater than the diameter of the valve assembly/frame in the compressed state.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Figure 1:
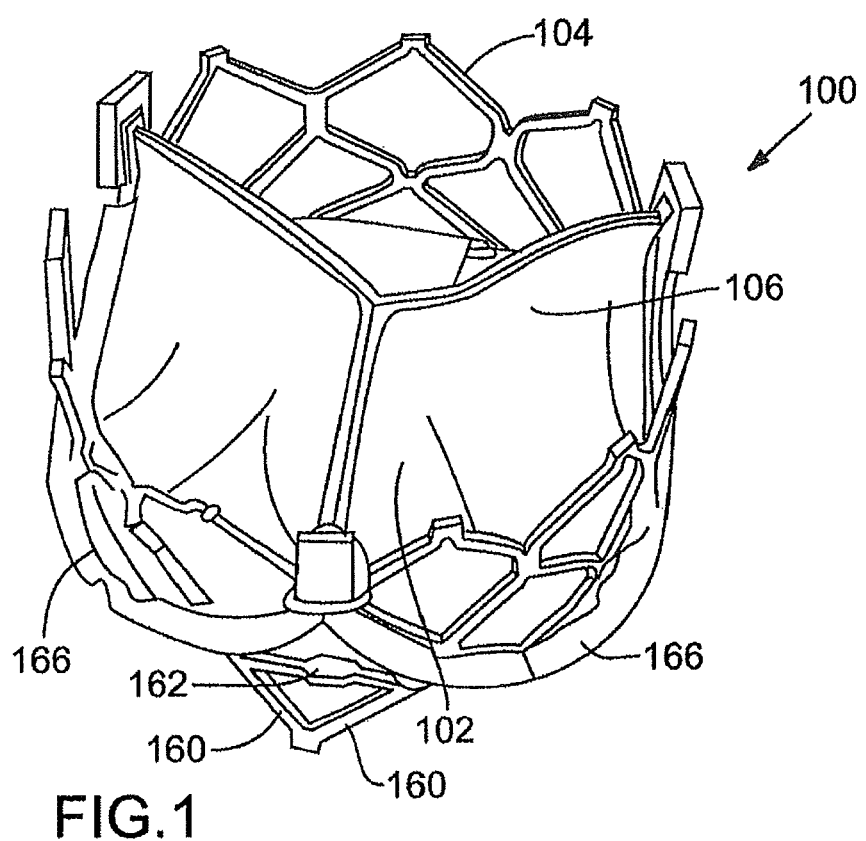
FIG. 1 is a perspective view of one embodiment of a prosthetic valve.

FIG. 1 shows a perspective view of an implantable prosthetic valve 100 (hereinafter "valve 100"), suitable for percutaneous deployment and configured to replace a diseased native valve in a patient. As discussed in more detail below, valve 100 can include a generally cylindrical support frame, such as a stent, which is compressible and/or foldable to a smaller delivery diameter, and a plurality of flexible leaflets releasably attached to the support element.

The valve 100 in the illustrated embodiment comprises a flexible membrane, or leaflet assembly, 102 mounted on an expandable, annular support stent, or frame, 104. As discussed in more detail below, frame 104 can comprise one or more scalloped portions 166 to which the flexible membrane is attached.

Valve 100 is desirably adapted to be radially collapsed or compressed to facilitate navigation through the narrow passages of a patient's vasculature to the treatment site within the patient's body. After valve 100 reaches the treatment site (e.g., the aortic valve annulus), valve 100 can be expanded within the orifice. To achieve the radial compression of the valve 100, frame 104 desirably comprises a collapsible and/or compressible support structure.

Flexible membrane 102 can be attached to frame 104 so that the flexible membrane 102 permits fluid flow through the valve 100 in one direction along a structural axis of the frame 104 and resists fluid flow in the opposite direction. In particular, the implantable structure supports flexible leaflets that allow a forward flow through the valve prosthesis and prevent a reverse flow as the flexible leaflets collapse inwardly to block the reverse flow. To provide for such fluid flow, flexible membrane 102 can comprise a collapsible pliant material formed as flexible leaflets 106 that are arranged to collapse in a tricuspid arrangement. Alternatively, the flexible membrane can be formed into other configurations, including, for example, a mono cusp or bicuspid configuration. Flexible leaflets 106 can comprise three pieces of pliant material that are connected to each other at seams (also referred to as commissure tabs) to form the flexible membrane.

The flexible membrane 102 can be made from biological matter, such as natural tissue, pericardial tissue (such as bovine, procine or equine pericardium), a harvested natural valve or other biological tissue. Alternatively, the valve member 102 can be made from biocompatible polymers or similar materials. Various flexible leaflet configurations and materials for constructing such leaflets are described in U.S. Pat. No. 6,730,118, U.S. Pat. No. 6,767,362, and U.S. Pat. No. 6,908,481, each of which is incorporated by reference herein.

As discussed above, frame 104 can comprise, for example, stent that has a generally cylindrical framework that can be expanded at a treatment site to secure valve 100 within or adjacent to the defective valve annulus. Frame 104 can also provide stability to the valve 100 and prevent the valve 100 from migrating after it has been implanted. Frame 104 can be a self-expanding frame or it can be expandable by a balloon member or other mechanical means. Frame 104 can be made from any of various suitable expandable and/or elastic materials and is typically made of a metal, such as stainless steel, CoCr alloys, titanium, or other biocompatible metals. Frame 104 also can be made from self expandable shape memory alloys, such as nickel titanium (NiTi) shape memory alloys, as marketed, for example, under the trade name Nitinol.

Figure 2:
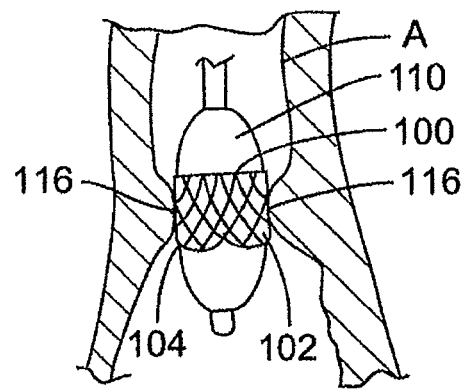
FIG. 2 is a schematic illustration of one embodiment of a prosthetic valve mounted to a balloon and deployed within a patient.

FIG. 2 is a schematic illustration of a flexible membrane 102 coupled to a frame 104 that is mounted on an inflatable balloon 110 of a balloon catheter for delivery and deployment of valve 100. Valve 100 can be initially crimped to a smaller radial profile on balloon 110 so that is presents a narrower cross-sectional profile to facilitate percutaneous delivery of the valve 100 to the treatment site. FIG. 2 illustrates the valve 100 being deployed in the aorta A at the aortic annulus 116 to replace a diseased or damaged native aortic valve. However, it should be understood that the prosthetic valves described herein can be implanted in other channels or orifices in the body using the same techniques as the one used for the implantation of the aortic valve prosthesis. Such an implantation may, for example, include the implantation of: valves in the veins (for instance a cardiac valve), valves in the esophagus and/or at the stomach, valves in the ureter and/or the vesica, valves in the biliary passages, valves in the lymphatic system, and valves in the intestines.

In one embodiment, a delivery catheter can advance valve 100 (mounted on balloon 110) through an introducer sheath and into the vasculature of a patient. The delivery catheter can then be advanced over a guidewire to move valve 100 to a target location in a body duct, such as the aortic annulus 116 of aorta A (FIG. 2). After the valve 100 is properly positioned at the treatment site, balloon 110 can be inflated to expand frame 104 radially to the desired size, securing valve 100 at the treatment site. It should be understood that valve 100 can also be deployed using a non-inflatable, mechanical embodiment of the delivery catheter or, alternatively, valve 100 can be a self-expanding valve.

Figure 3:
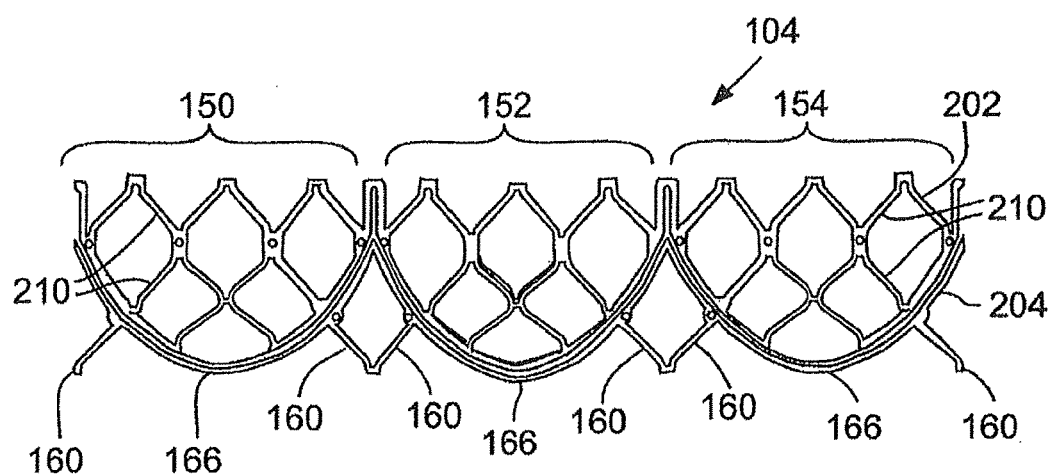
FIG. 3 is a flattened view of one embodiment of a frame of a prosthetic valve.

In one embodiment, frame 104 can comprise one or more scalloped portions 166 at a lower portion of frame 104. FIG. 3 illustrates, for convenience, a flattened schematic view of a frame 104 that comprises a plurality of frame sections 150, 152, 154, which each have a respective scalloped portion 166 at a lower portion of frame 104. Frame sections 150, 152, 154 can comprise a plurality of struts (or strut sections) 160, 210. Adjacent scalloped portions 166 can be connected together by struts 160. Because the frame is shown in a flattened view, the two end strut sections 160 of FIG. 3 appear to be disconnected; however, the two end strut sections 160 are desirably connected to one another, in the same manner of the other strut sections 160 shown in FIG. 3.

Referring again to FIG. 1, if desired, an expansion restriction member 162 can be secured between two adjacent strut sections 160. Expansion restriction member 162 can be, for example, a suture or thread that is secured to adjacent strut sections 160 to prevent the valve 100 from being over-expanded during deployment.

Figure 4:
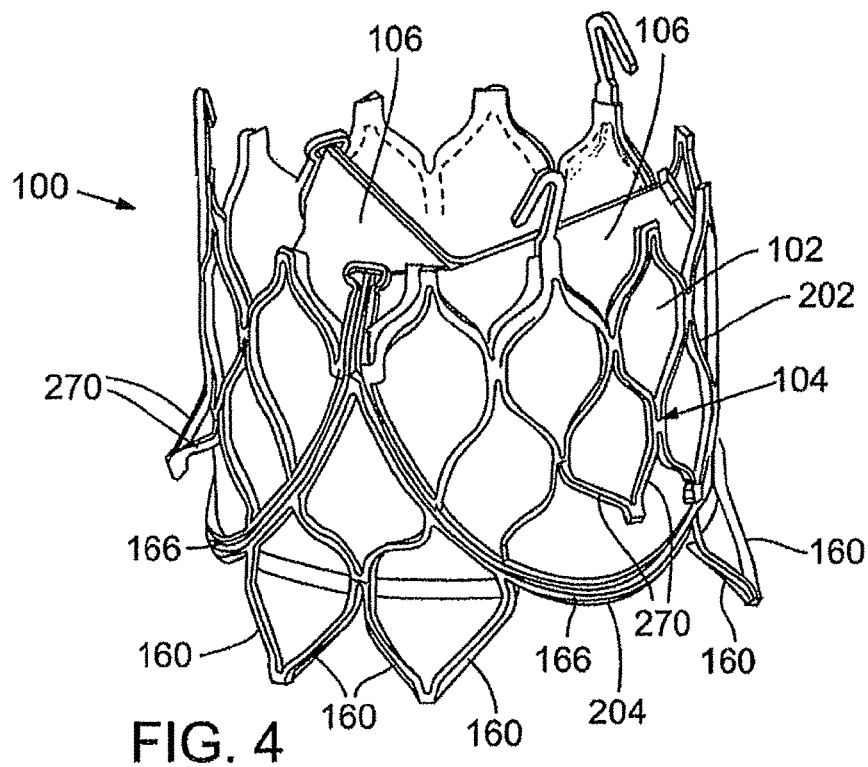
FIG. 4 is a perspective view of one embodiment of a prosthetic valve.

FIG. 4 illustrates a valve 100 with a frame 104 that has a plurality of scalloped portions 166. Frame 104 comprises a collapsible frame with a flexible membrane 102 attached thereto. As noted above, strut sections 160 desirably extend from a portion of the scalloped frame to provide structural strength to the frame 104. The number of strut sections 160 between adjacent scalloped portions 166 can vary. For example, FIG. 3 shows two strut sections 160 (forming one cell) between adjacent scalloped portions 166, while FIG. 4 shows four strut sections 160 between adjacent scalloped portions 166 (arranged to form three cells between adjacent scalloped portions). Strut sections 160 can also extend radially outward from the frame 104, as shown in FIG. 4, to help anchor the valve 100 in the body and to help prevent migration or movement of the valve after it has been deployed within the body. Other portions of the frame 104 can also be configured to extend radially outward to help anchor the valve in place. For example, certain cell struts, such as cell struts 270 (FIG. 4), can be configured to extend radially outwards from the frame 104 to provide additional valve anchoring means.

Figure 5:
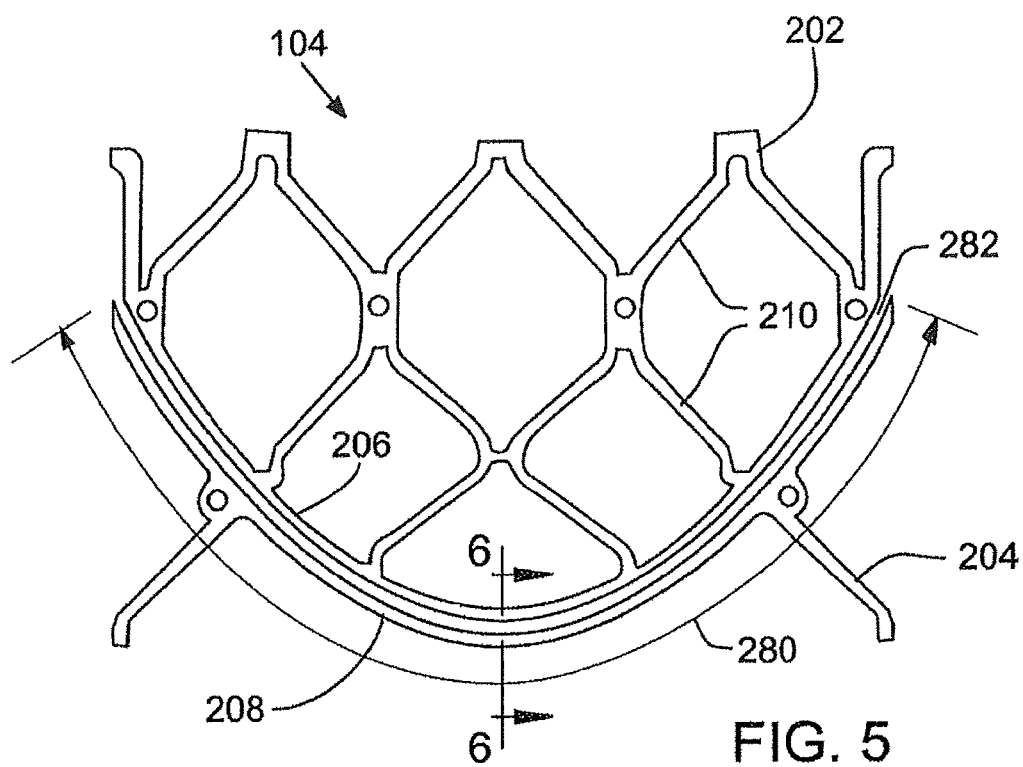
FIG. 5 is a flattened view of one embodiment showing a portion of a frame of a prosthetic valve.

As best shown in FIG. 5, a frame 104 can be comprised of a first or "upper" part 202 and a second or "lower" part 204. First part 202 can include a plurality of struts or strut sections 210 and a first arc section 206. Second part 204 includes a second arc section 208. Both arc sections 206, 208 desirably have an arc length 280 that is substantially the same. First part 202 and second part 204 are desirably separate elements that are not connected to each other by any strut members of the frame 104. Accordingly, as shown in FIG. 5, when first part 202 is positioned adjacent second part 204, a gap (or opening) 282 is defined between the two parts. A flexible membrane 102 or portions thereof can be received into gap 282 to facilitate attachment of the flexible membrane 102 to the frame 104. The two surfaces facing gap 282 include a first leaflet receiving surface (e.g., the lower surface of upper part 202) and a second leaflet receiving surface (e.g., the upper surface of lower part 204). If desired, the first part 202 and second part 204 can be connected via one or more connecting struts 268 (FIG. 17) to provide additional structural strength to the frame 104.

Figure 7:
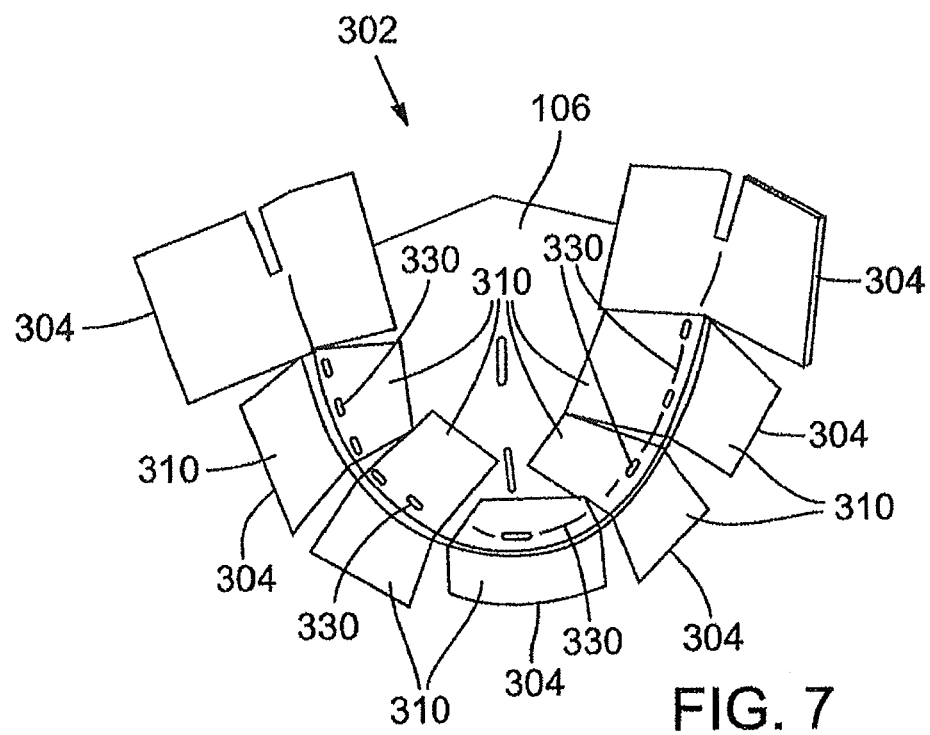
FIG. 7 is a perspective view of an embodiment of a flexible leaflet with one or more cloth portions sewn to the leaflet.
Figure 8:
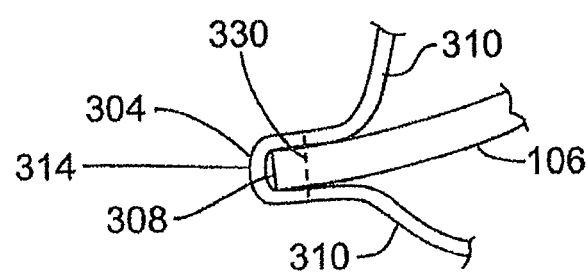
FIG. 8 is a simplified sectional side view of a portion of the flexible leaflet and cloth shown in FIG. 7.

In one embodiment, the flexible leaflets 106 of the flexible membrane 102 can be received in the gap 282 and the first and second arc sections 206 and 208 can help secure the flexible leaflets to the frame 104 and/or provide a point of attachment. Referring to FIGS. 7 and 8, a cloth member 304 is desirably attached to a flexible leaflet 106. FIG. 7 is a perspective view of a leaflet sub-assembly 302 in which one or more portions of cloth 304 are attached to selected portions of flexible leaflet 106. Leaflet sub-assembly 302 can be formed by attaching cloth 304 to flexible leaflet 106 by sewing (suturing) or other suitable attachment means. The cloth 304 can be any fabric or other material made from any of various suitable biocompatible synthetic materials, such as woven polyester, polyethylene terephthalate (PET), or polytetrafluoroethylene (PTFE).

Figure 6:
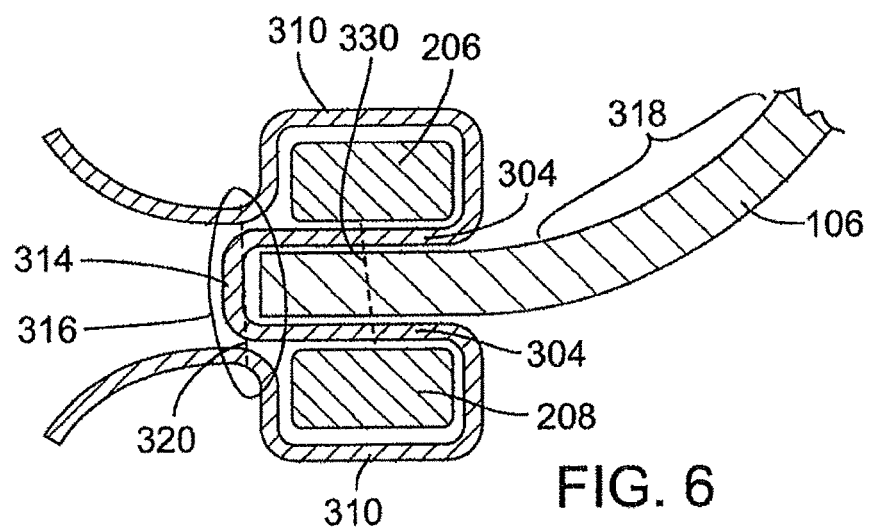
FIG. 6 is a cross-section view taken along line 5-5 in FIG. 5, with a leaflet attachment portion included.

To attach cloth 304 to the leaflet 106, a cloth portion 304 can be folded over a lower edge portion 308 (FIG. 8) of leaflet 106, and cloth 304 and leaflet 106 can be sewn together along a leaflet—cloth suture line 330 (hereinafter "suture line 330"). In this manner, leaflet edge 308 is captured between two layers of cloth 304 to form a leaflet attachment portion 314 (FIG. 6). Excess portions 310 of cloth 304 extend along both sides of flexible leaflet 106 away from suture line 330 and away from edge 308. As described in more detail below, excess cloth portions 310 can be used to secure the flexible leaflets 106 to the frame 104. If desired, a plurality of separate cloth portions 304 (as shown in FIG. 7) can be attached to the leaflet 106. In this manner, when the leaflet is secured to the frame between the first and second arc sections 206, 208, the separate cloth portions 304 can extend between the struts that extend from the first arc section 206.

Referring now to FIG. 6, a method of attaching leaflet sub-assembly 302 to frame 104 is described. FIG. 6 is a simplified cross-sectional view of a leaflet sub-assembly attached to a frame. In particular, leaflet sub-assembly 302 extends radially between and is "sandwiched" or otherwise captured between first arc section 206 (of the first part 202 of the frame) and second arc section 208 (of the second part 204 of the frame). As shown in FIG. 6, leaflet sub-assembly 302 can be positioned between the two arc sections so that suture-line 330 is substantially captured between the two arcs. Additionally, an edge portion 314 comprised of two layers of cloth and a portion of the leaflet desirably extends radially outwards from between the first and second arc sections 206 and 208.

As illustrated in FIG. 6, excess cloth portions 310 of cloth 304 can be wrapped over and around first arc section 206 and second arc section 208. In this embodiment, excess portions 310 of cloth 304 can be sewn together within an attachment area 316. Attachment area 316 is desirably located outside of (e.g., radially external to) frame 104. For example, a sandwiching suture line 320 can pass through the two ends of excess cloth portions 310 and also through the edge portion 314 that extends out from between first and second arc sections 206 and 208. Thus, by securing the flexible leaflet to the cloth and then securing portions of the cloth to itself, the flexible leaflet 106 can be securely attached to the frame 104 without requiring additional sutures passing through the flexible leaflet 106. If desired, leaflet 106 can be positioned so that suture line 320 passes through the excess cloth portions 310 and through the leaflet 106.

Conventional frames typically require suturing the flexible membranes at the commisures directly to vertical posts. However, the suture line applies local stress and abrasion on the leaflet which may lead to early leaflet failure. Accordingly, this approach causes very high stresses on the commissures when the flexible leaflets move between open and closed positions.

Figure 9A:
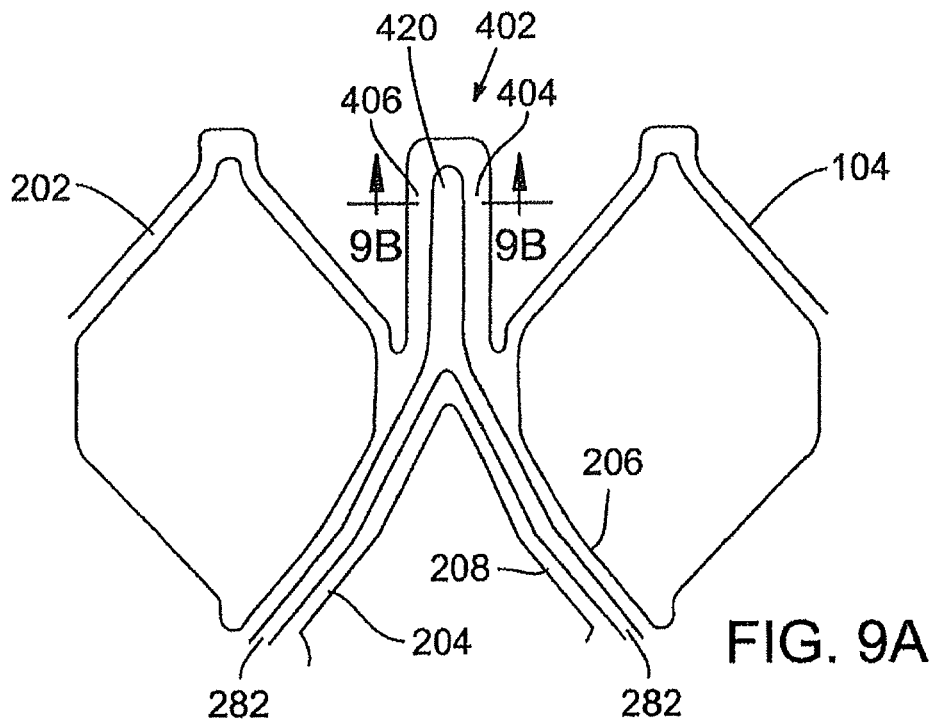
FIG. 9A is a flattened view of one embodiment showing a portion of a frame of a prosthetic valve.
Figure 9B:
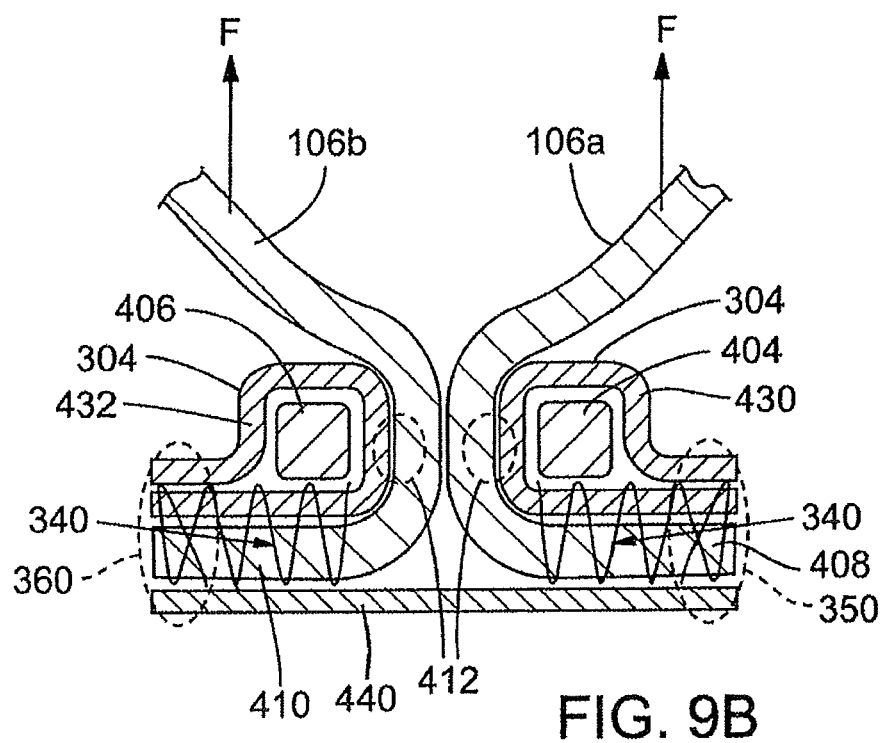
FIG. 9B is a cross-section view taken along line 9B-9B in FIG. 9A, with two leaflet attachment portions included.

FIGS. 9A and 9B illustrate a method of attaching flexible leaflets to a frame without suturing the flexible valves directly to vertical posts. FIG. 9A illustrates an upper portion 402 of frame 104 where two leaflets come together in the valve (e.g., the commissure). At the commissure, first frame part 202 has a first vertical strut 404 and a second vertical strut 406. First strut 404 and second strut 406 are spaced apart and define an opening 420 therebetween for receiving at least a portion of two adjacent flexible leaflets 106.

FIG. 9B is a cross-section view taken along line 9B-9B in FIG. 9A, with flexible leaflets and cloth portions shown positioned between the first and second struts 404, 406. As shown in FIG. 9B, two flexible leaflets 106a and 106b can be inserted and captured between first and second struts 404 and 406. Flexible leaflet 106a, 106b can be attached to a respective cloth 304, creating an area 408 where the leaflet 106a is attached to the cloth 304 and an area where the leaflet 106a is not attached to the cloth 304. Leaflet 106a can be wrapped around at least a portion of first strut 404 so that the unattached portion of the leaflet 106a extends radially inwards into the interior of the frame. The unattached portion of cloth 304 can form an excess cloth portion 430 that extends radially inward into the frame and wraps back around the strut 404.

Similarly, leaflet 106b can be attached to a cloth 304, creating an area 410 where the leaflet 106b is attached to the cloth 304 and an area where the leaflet 106b is not attached to the cloth 304. Leaflet 106b can be wrapped around second strut 406 so that the unattached portion of the leaflet 106b extends radially inwards into the interior of the frame. The unattached portion of cloth 304 can form an excess cloth portion 432 that extends inward into the frame and wraps back around the strut 406.

To secure the leaflets 106a, 106b to the frame, another piece of cloth 440 can be placed radially outside of the frame and positioned over the portion of flexible leaflets 106a, 106b that extend radially outside of the frame (e.g., the portions of 408, 410 that are external to struts 404, 406). The second piece of cloth 440 can be sewn to the leaflet 106a at an attachment area 350 to secure the leaflets to first strut 404. Thus, the second piece of cloth 440 can be sewn (or otherwise attached) to leaflet 106a, the portion of cloth 304 attached to leaflet 106a, and to the excess cloth portion 430 that has been wrapped around first strut 404. The second piece of cloth 440 can similarly be sewn to the leaflet 106b, the portion of cloth 304 attached to leaflet 106b, and to the excess cloth portion 432 (which has been wrapped around second strut 406) at an attachment area 360 to secure the leaflets to second strut 406.

Operationally, when flexible leaflets 106 are closed, load F is applied to the leaflets to move them radially inward as shown in FIG. 9B. Folding flexible leaflets 106 around stent struts 404 and 406 can reduce stresses on the leaflets by creating a friction attachment at leaflet-strut contact areas 412, which reduces the stresses at suture lines 340. Furthermore, as discussed in more detail below, by securing the leaflets 106a, 106b at attachment areas 350, 360 on the outer side of frame 104, relative movement at the leaflet/frame interface can be reduced or eliminated, which further reduces stresses and strains on the leaflets during expansion and/or compression of the valve 100.

Figure 10:
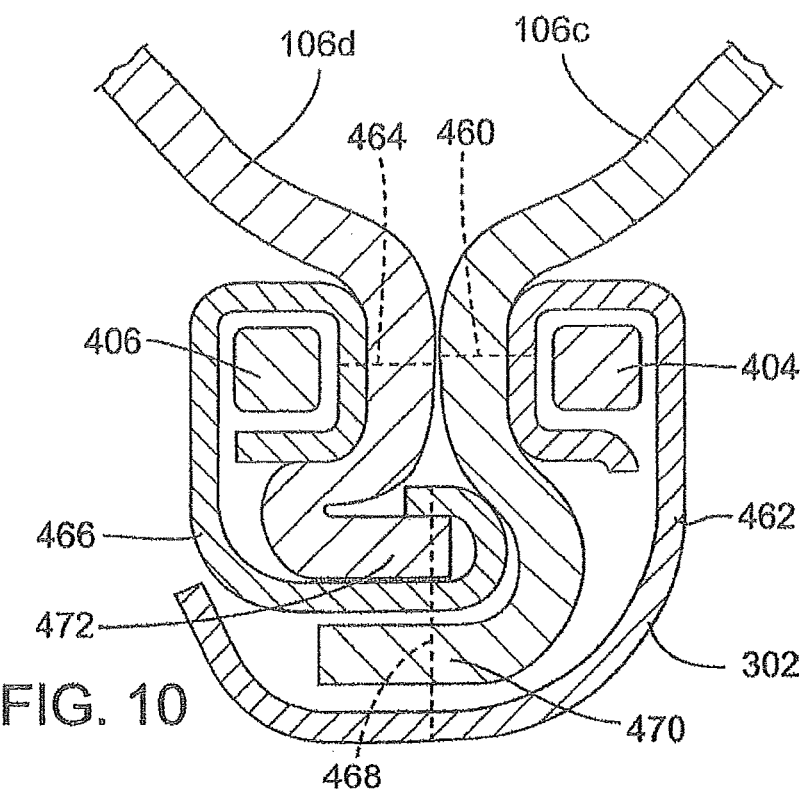
FIG. 10 is a cross-section view showing another embodiment of a portion of a prosthetic valve having two leaflet attachment portions attached to a portion of a frame.

FIG. 10 shows another embodiment by which flexible leaflets 106c, 106d can be attached to first and second struts 404 and 406 of a frame 104. Similar to the embodiment shown in FIG. 9B and described above, a first leaflet 106c is secured to a cloth 304 by a suture 460 and an excess cloth portion 462 extends inwardly of the frame and wraps back around first strut 404 to extend back outwardly of the frame. A second leaflet 106d is secured to a cloth 304 by a suture 464 and an excess cloth portion 466 extends inwardly of the frame and wraps back around second strut 406 to extend back outwardly of the frame. After the excess portions of cloth 462, 466 are wrapped back around first and second struts 404, 406, they can be secured to one another by another suture 468 at an area outside of the frame 104. As shown in FIG. 10, suture 468 can pass through both of the excess cloth portions 462, 466 and through portions of the leaflets (e.g., leaflet portions 470, 472) that extend outward from between the first and second struts 404, 406. In addition, if desired, the excess cloth portions and/or flexible leaflets can be folded and/or wrapped around each other so that the suture 468 extends through one or more portions of the excess cloth portions and/or the flexible leaflets.

Figures 11, 12, 13:
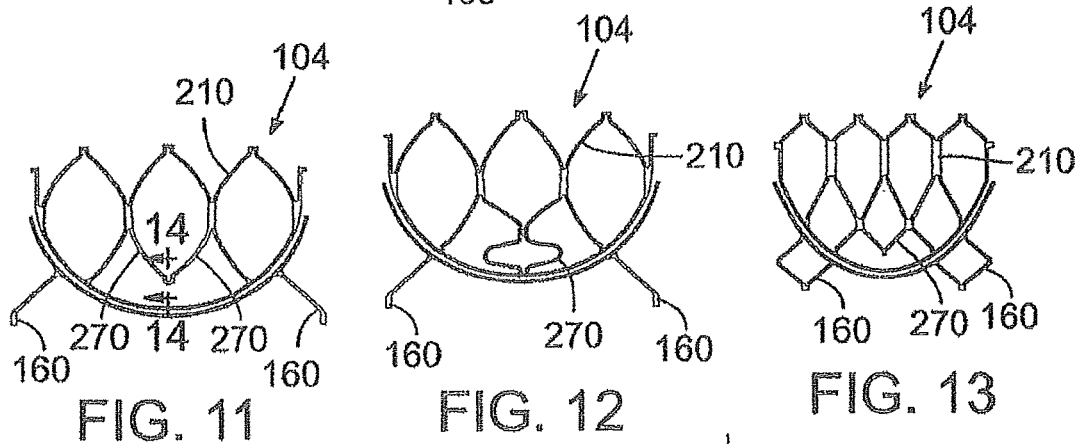
FIG. 11 is an embodiment of another portion of a frames of a prosthetic valve.
FIG. 12 is an embodiment of another portion of a frames of a prosthetic valve.
FIG. 13 is an embodiment of another portion of a frames of a prosthetic valve.

FIGS. 11-13 show additional embodiments of frames 104 that have scalloped portions. In particular, FIGS. 11-13 illustrate alternative shapes and configurations of struts 210, 270. The shape and number of struts can vary. For example, struts 210 can be configured to be substantially straight (FIG. 13), or they can be rounded or curved (FIG. 12).

Figure 14:
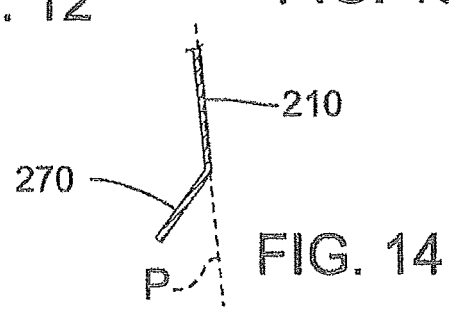
FIG. 14 is a cross-section view taken along line 14-14 in FIG. 11.

As described above with regard to FIG. 4, the struts or other frame members can also be configured to extend radially outward of the generally cylindrical surface of the expandable framework to improve the ability to anchor the frame to the tissue. For example, as best seen in FIGS. 4, 11, and 14, struts 160 and/or 270 may be bent so that they protrude outward from stent struts 210 (i.e., radially outward from the tangential plane P defined on an external surface of the cylindrically shaped frame 104). Similarly, in the embodiments illustrated in FIGS. 12 and 13, struts 160 and/or 270 can be formed so that one or more of struts 160 and/or 270 extend radially outward from the frame 104.

The use of the scalloped frame 104 together with the methods of attachment described herein beneficially enable the flexible membrane and flexible leaflets to be secured to a frame without introducing needle holes and/or sutures in the area where a leaflet flexes (e.g., leaflet flexing area 318 shown in FIG. 6) or undergoes significant stresses. Leaflets are particularly susceptible to failure at areas where they flex and by reducing and/or eliminating needle holes in the leaflets at these areas, the structural integrity of the flexible leaflets can be improved. Thus, in contrast to traditional methods of attachment where a flexible membrane is simply sutured to a frame, the methods of attachment described herein eliminate and/or reduce needle holes and sutures in the leaflet flexing area 318, which increases the durability of the valve.

In addition, the leaflet can be attached to the frame along the length of the first and second arc sections 206 and 208. By capturing the entire edge 308 (or substantially the entire edge) of flexible leaflet 106 between the arc sections 206 and 208 and securing the leaflet to the arc sections as described herein, the leaflet stresses can be optimally distributed along the length of the leaflet edge.

In addition, the methods described herein are particularly useful to facilitate attaching a flexible membrane to a frame while the valve is in a partially collapsed (partially-crimped) configuration. As described in U.S. Patent Publication 2008/0154355, the entire disclosure of which is incorporated by reference herein, it can be desirable to attach a flexible membrane to a partially collapsed frame, which can allow the frame to be constructed with relatively large angles between adjacent struts to enhance the structural rigidity of the frame. Due to the enhanced structural rigidity, the frame can be constructed with thinner metal struts, which can allow the frame to be crimped to a smaller profile. However, it can be difficult to attach a flexible membrane to a frame in a partially collapsed state because the diameter of the flexible membrane is greater than the diameter of the partially collapsed frame. For instance, in certain implementations, the diameter of the valve member can be twice that of the partially collapsed frame. The valve member therefore cannot easily conform to the shape of the partially collapsed frame, and as a result, assembly of the valve assembly is rendered more difficult.

The frames described herein can easily and accurately receive flexible membranes while the frames are in a partially collapsed configuration. In addition, by reducing the relative movement that occurs between the frame and the flexible leaflets during expansion of the valve at the treatment site, the valves produced by the methods describe herein have increased strength and durability.

Referring again to FIG. 5, first and second arc sections 206 and 208 are substantially the same length (e.g., arc length 280). The length of the first and second arc sections 206, 208 desirably can be selected to correspond to the length of a similarly scalloped shaped edge portion of a leaflet. Thus, as described herein, the accurate assembly of the scalloped-shaped leaflet 106 between the two arc sections 206, 208 can be achieved. In addition, the attachment of the leaflet 106 to the arc sections 206, 208 can be easily and accurately performed even if the frame 104 is in a crimped (folded) or partially crimped configuration due to the fact that the arc length of sections 206, 208 where the leaflet is attached remains constant when the frame is compressed.

Figure 15:
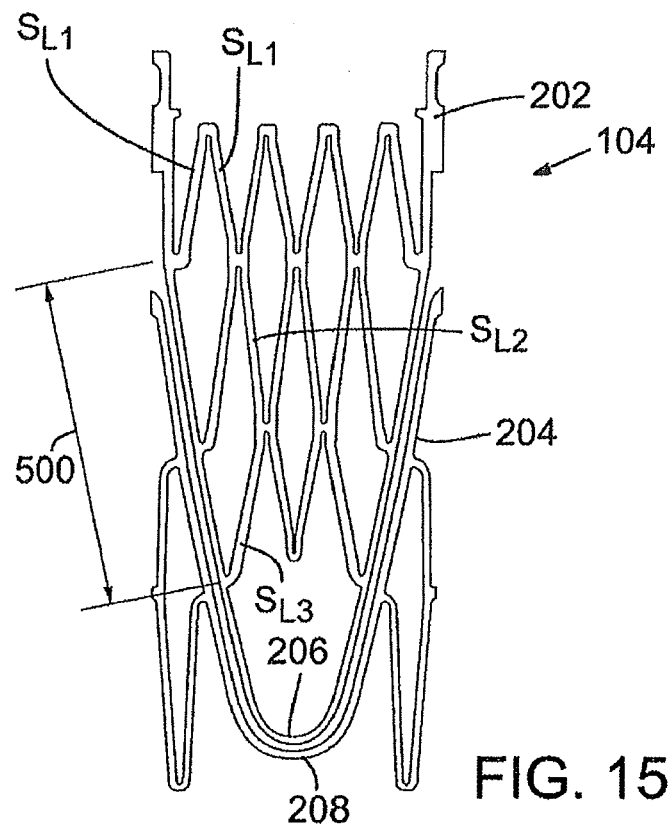
FIG. 15 is a view of an embodiment of a frame, with the frame shown in a crimped or partially crimped configuration.
Figure 16:
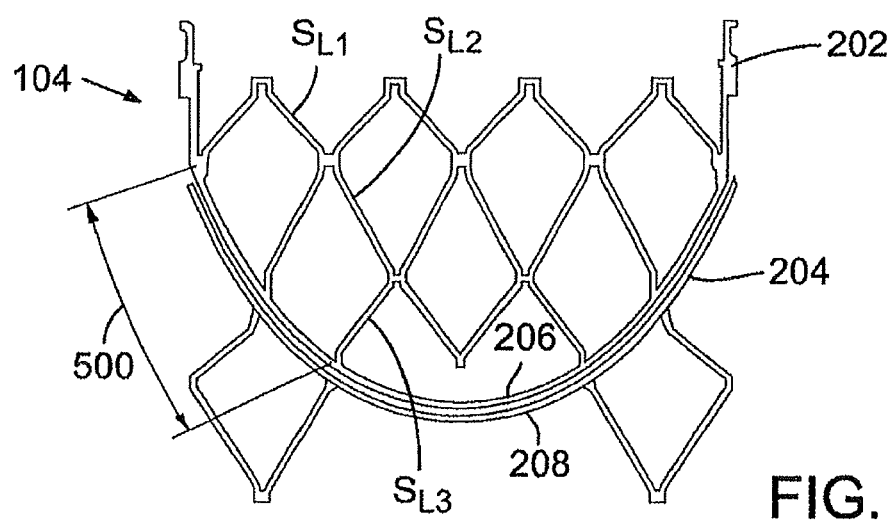
FIG. 16 is a view of the frame shown in FIG. 15 in an expanded (or uncrimped) configuration.

FIGS. 15 and 16 illustrate a segment of a frame that is configured to expand from a reduced profile (FIG. 15) to an expanded profile (FIG. 16) while maintaining the relationship between first and second arc sections 206, 208. In particular, the length of corresponding portions of first and second arc sections 206, 208 are desirably matched to the lengths of related struts SL1, SL2, and SL3. For example, as shown in FIGS. 15 and 16, arc section 500 can be defined by the length of arc section 206 between two strut members extending therefrom (e.g., SL1 and SL3). Arc section 500 can be configured to have substantially the same length as the combined length of one or more struts. In particular, Arc section 500 is configured to be substantially the same length as the combined length of struts SL2 and SL3.

After flexible leaflets are attached to the frame, the frame can expand smoothly and evenly from a reduced profile (FIG. 15) to an expanded profile (FIG. 16), causing arc sections 206, 208 to also expand evenly. This even expansion from a first profile to a second profile reduces relative movement between the arc sections, which, in turn, reduces stress on the leaflets that are attached to the arc sections. Moreover, because the length of the struts are matched to corresponding lengths of sections of the first and second arc sections 206, 208, relative movement between the frame and flexible leaflets is reduced in all configurations and stages of crimping and/or expansion. Thus, a flexible leaflet can be attached to the frame shown in FIG. 15 and then, if desired, the frame can be crimped (or folded) to an even smaller profile without causing additional stresses at the leaflet attachment area.

In prior art implantable valve devices, during deployment, the dimensions of the complete, implantable structure of the implantable valve vary from its initial first crimped position to its final deployed position. Thus, typically when attaching flexible leaflets to the implantable structure one should take into consideration the dimension changes and leave "slack" or extra leaflet material so that upon deployment of the valve device the flexible leaflets do not tear or deform. By maintaining a constant arc length of the arc sections during deployment of valve 100, there is no need for "slack" material in the flexible leaflets 106. Instead, the attachment points of the flexible leaflets 106 remain at a constant distance regardless of the delivery position of valve 100 (crimped or expanded).

Figure 17:
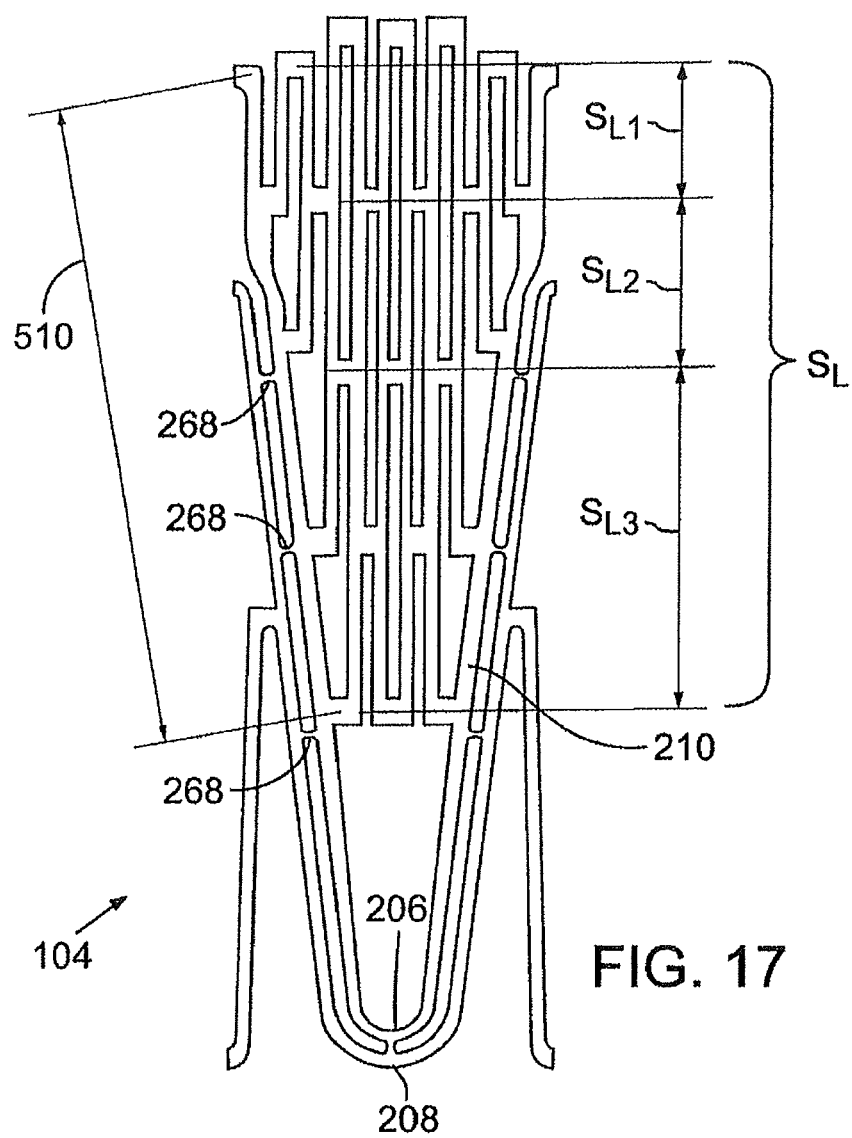
FIG. 17 is a view of another embodiment of a frame, with the frame shown in a crimped or partially crimped configuration.

Referring to FIG. 17, another embodiment of a frame 104 is disclosed. FIG. 17 shows a section of a compressed frame that comprises first arc section 206 and second arc section 208, with the two arc sections being connected via optional connecting struts 268. As described above with regard to FIGS. 15 and 16, relative movement between the first and second arc sections 206, 208 can be avoided by matching arc sections with strut sections so that the first arc section 206 and second arc section 208 remain constant during deployment, providing a stable area for anchoring flexible leaflets 106. As shown in FIG. 17, in this embodiment, the arc length of arc section 510 is matched to the total length SL of cell struts SL1, SL2, and SL3. That is, the total length SL (SL1+SL2+SL3) of the strut sections is substantially the same as the length of arc section 510. Because the geometrical constraint on length SL of cell struts 210 is designed such that cell struts 210 may be collapsed and expanded without changing the dimensions of the first and second arc sections 206 and 208, the frame 104 can be evenly crimped and/or expanded, which allows flexible leaflets 106 to also deploy evenly.

In embodiments disclosed above, little or no relative movement exists between the flexible leaflets 106 and attachment points on the first and second arc sections 206 and 208. As a result, the valve has greater durability and is capable of withstanding the harsh conditions prevailing within the vasculature and especially the millions of cycles of stress applied by the blood pressure.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. An implantable prosthetic valve, comprising:
 a radially collapsible and expandable annular frame comprising a plurality of struts and having an upper end and a lower end, wherein the struts are arranged to form a plurality of circumferentially extending rows of closed cells, including an uppermost row of closed cells defining the upper end of the frame; and
 a leaflet structure positioned within the frame, the leaflet structure comprising a plurality of leaflets each comprising two opposing leaflet side portions, each leaflet side portion being paired with an adjacent leaflet side portion of an adjacent leaflet to form commissures of the leaflet structure;
 wherein the frame comprises a pair of vertical posts adjacent each of the commissures, the vertical posts of each pair being parallel to each other and spaced apart from each other so as to define an opening therebetween, wherein the vertical posts of each pair are connected to each other at their upper ends, and wherein the pairs of vertical posts have respective lower ends that are axially spaced from the lower end of the frame;
wherein the pairs of vertical posts are positioned axially along the frame entirely within the uppermost row of closed cells, and the pairs of vertical posts are circumferentially spaced apart from each other by a plurality of closed cells of the uppermost row of closed cells;
wherein the uppermost row of closed cells is formed partly by an uppermost, circumferentially extending row of angled struts of the frame interconnecting adjacent pairs of vertical posts, wherein the angled struts of the uppermost row of angled struts are connected to each other at their upper ends by U-shaped connection portions, and wherein each U-shaped connection portion forms a gap between adjacent upper ends of a corresponding pair of angled struts;
wherein each pair of leaflet side portions extends radially outwardly through the opening of a respective pair of vertical posts, with one of the leaflet side portions wrapping around at least a portion of one of the vertical posts at a location outside of the frame and the other leaflet side portion wrapping around at least a portion of the other vertical post at a location outside of the frame; and
wherein each commissure comprises a cloth portion positioned radially outward of the frame at each pair of vertical posts and radially outward of the leaflet side portions that are wrapped around the vertical posts, the cloth portion also being sutured to the leaflet side portions that are wrapped around the vertical posts.

2. The implantable prosthetic valve of claim 1, wherein each leaflet has a scalloped shaped lower edge portion secured to the frame.

3. The implantable prosthetic valve of claim 2, further comprising additional cloth portions sutured to opposite surfaces of the lower edge portion of each leaflet.

4. The implantable prosthetic valve of claim 1, wherein the cloth portion of each commissure comprises a first cloth portion and each commissure further comprises second and third cloth portions, the second cloth portion wrapping around at least a portion of one of the vertical posts and the third cloth portion wrapping around at least a portion of the other vertical post, each of the second and third cloth portions being sutured to the first cloth portion and one of the leaflet side portions that is wrapped around one of the vertical posts.

5. The implantable prosthetic valve of claim 4, wherein each of the second and third cloth portions of each commissure is wrapped completely around a respective vertical post and is sutured to itself as well as an adjacent leaflet side portion that is wrapped around the same vertical post.

6. The implantable prosthetic valve of claim 1, wherein:
the frame comprises an upper frame section and a lower frame section, the upper frame section having a plurality of struts and a first leaflet receiving surface at a lower portion of the upper frame section, the lower frame section having a second leaflet receiving surface at an upper portion of the lower frame section; and
each leaflet comprises a lower edge portion disposed between the first and second leaflet receiving surfaces.

7. The implantable prosthetic valve of claim 6, wherein the first and second leaflet receiving surfaces are scalloped shaped.

8. The implantable prosthetic valve of claim 1, wherein the leaflets have scalloped shaped lower edge portions secured to the frame, and wherein the implantable prosthetic valve further comprises additional cloth portions wrapped around the lower edge portions of the leaflets.

9. The implantable prosthetic valve of claim 1, wherein each U-shaped connection portion comprises two vertical surfaces and a lateral surface extending between the two vertical surfaces, wherein the vertical surfaces are parallel to a central longitudinal axis of the prosthetic valve, wherein the lateral surface extends between and interconnects upper ends of the vertical surfaces, and wherein the vertical surfaces are spaced apart from each other to define the gap of the U-shaped connection portion.

10. The implantable prosthetic valve of claim 1, wherein:
the frame comprises an upper frame section and a lower frame section, the upper frame section having a plurality of struts and a scallop-shaped lower edge, the lower frame section having a scallop-shaped upper edge;
wherein the lower edge of the upper frame section and the upper edge of the lower frame section are spaced apart to define a leaflet-receiving opening;
wherein the leaflet-receiving opening extends continuously between adjacent pairs of vertical posts; and
each leaflet comprises a lower edge portion disposed within the leaflet-receiving opening.

11. A method of assembling an implantable prosthetic valve comprising:
providing a radially collapsible and expandable annular frame comprising a plurality of struts and having an upper end and a lower end, wherein the struts are arranged to form a plurality of circumferentially extending rows of closed cells, including an uppermost row of closed cells defining the upper end of the frame, the frame comprising a plurality of circumferentially spaced pairs of vertical posts, the vertical posts of each pair being parallel to each other and spaced apart from each other so as to define an opening therebetween, wherein the vertical posts of each pair are connected to each other at their upper ends, wherein the pairs of vertical posts have respective lower ends that are axially spaced from the lower end of the frame, wherein the pairs of vertical posts are positioned axially along the frame entirely within the uppermost row of closed cells and the pairs of vertical posts are circumferentially spaced apart from each other by a plurality of closed cells of the uppermost row of closed cells, wherein the uppermost row of closed cells is formed partly by an uppermost, circumferentially extending row of angled struts of the frame interconnecting adjacent pairs of vertical posts, wherein the angled struts of the uppermost, circumferentially extending row of angled struts are connected to each other at their upper ends by U-shaped connection portions, wherein each U-shaped connection portion forms a gap between adjacent upper ends of a corresponding pair of angled struts;
providing a leaflet structure comprising a plurality of leaflets each comprising two opposing leaflet side portions;
inserting a pair of adjacent leaflet side portions through the opening of each pair of vertical posts in a radially outward direction;
wrapping one leaflet side portion of each pair of adjacent leaflet side portions at least partially around one of the vertical posts and wrapping the other leaflet side portion of each pair of adjacent leaflet side portions at least partially around the other vertical post; and suturing a cloth portion to each pair of adjacent leaflet side portions at a location outside of the frame and radially outward of the adjacent leaflet side portions that are wrapped around the vertical posts.

12. The method of claim 11, further comprising suturing additional cloth portions to opposite surfaces of a scalloped shaped lower edge portion of each leaflet.

13. The method of claim 12, further comprising securing the lower edge portion of each leaflet to the frame after suturing the additional cloth portions to the leaflets.

14. The method of claim 11, further comprising securing two additional cloth portions to each pair of adjacent leaflet side portions by wrapping the additional cloth portions at least partially around respective vertical posts and suturing them to the adjacent leaflet side portions.

15. The method of claim 14, wherein each additional cloth portion is wrapped completely around a respective vertical post and is sutured to itself as well as an adjacent leaflet side portion of a leaflet that is wrapped around the same vertical post.

16. An implantable prosthetic valve, comprising:
a radially collapsible and expandable annular frame comprising a plurality of struts and having an upper end and a lower end, wherein the struts are arranged to form a plurality of circumferentially extending rows of closed cells, including an uppermost row of closed cells defining the upper end of the frame; and
a leaflet structure positioned within the frame, the leaflet structure comprising a plurality of leaflets each comprising two opposing leaflet side portions, each leaflet side portion being paired with an adjacent leaflet side portion of an adjacent leaflet to form commissures of the leaflet structure;
wherein the frame comprises a pair of vertical posts adjacent each of the commissures, the vertical posts of each pair being parallel to each other and spaced apart from each other so as to define an opening therebetween, wherein the vertical posts of each pair are connected to each other at their upper ends, wherein the pairs of vertical posts have respective lower ends that are axially spaced from the lower end of the frame;
wherein the pairs of vertical posts are positioned axially along the frame entirely within the uppermost row of closed cells and the pairs of vertical posts are circumferentially spaced apart from each other by a plurality of closed cells of the uppermost row of closed cells;
wherein the uppermost row of closed cells is formed partly by an uppermost, circumferentially extending row of angled struts of the frame interconnecting adjacent pairs of vertical posts, wherein the angled struts of the uppermost, circumferentially extending row of angled struts are connected to each other at their upper ends by U-shaped connection portions, wherein each U-shaped connection portion comprises two vertical portions and a lateral portion extending between the two vertical portions, wherein the vertical portions are parallel to a central longitudinal axis of the prosthetic valve, wherein the lateral portion extends between and interconnects upper ends of the vertical portions, and wherein the vertical portions are spaced apart from each other to define a gap between the upper ends of a corresponding pair of adjacent angled struts; and
wherein each pair of leaflet side portions extends radially outwardly through the opening of a respective pair of vertical posts and are secured to the vertical posts outside of the frame.

17. The implantable prosthetic valve of claim 16, wherein for each pair of leaflet side portions and corresponding pair of vertical posts, one of the leaflet side portions wraps around at least a portion of one of the vertical posts at a location outside of the frame and the other leaflet side portion wraps around at least a portion of the other vertical post at a location outside of the frame.

18. The implantable prosthetic valve of claim 17, wherein each commissure comprises a cloth portion positioned radially outward of the frame at each pair of vertical posts and radially outward of the leaflet side portions that are wrapped around the vertical posts, the cloth portion also being sutured to the leaflet side portions that are wrapped around the vertical posts.

19. The implantable prosthetic valve of claim 16, wherein the plurality of circumferentially extending rows of closed cells includes additional rows of closed cells that are positioned axially below the uppermost row of closed cells and the pairs of vertical posts.

* * * * *